US007718698B2

(12) United States Patent
Breivik et al.

(10) Patent No.: US 7,718,698 B2
(45) Date of Patent: May 18, 2010

(54) PROCESS FOR DECREASING ENVIRONMENTAL POLLUTANTS IN AN OIL OR A FAT

(75) Inventors: Harald Breivik, Porsgrunn (NO); Olav Thorstad, Porsgrunn (NO)

(73) Assignee: Pronova Biopharma Norge AS, Baerum (NO)

( * ) Notice: Subject to any disclaimer, the term of this patent is extended or adjusted under 35 U.S.C. 154(b) by 0 days.

(21) Appl. No.: 12/113,356

(22) Filed: May 1, 2008

(65) Prior Publication Data
US 2008/0234375 A1 Sep. 25, 2008

Related U.S. Application Data

(63) Continuation of application No. 10/517,812, filed as application No. PCT/IB03/02827 on Jul. 8, 2003.

(30) Foreign Application Priority Data
Jul. 11, 2002 (SE) ..................... 0202188

(51) Int. Cl.
A61K 31/20 (2006.01)
(52) U.S. Cl. .................. 514/558; 426/601; 549/339; 554/175; 554/3; 554/121; 554/224
(58) Field of Classification Search .............. 554/175, 554/35, 121, 224; 514/558; 426/601; 549/399
See application file for complete search history.

(56) References Cited

U.S. PATENT DOCUMENTS

| 2,126,467 A | 8/1938 | Hickman et al. |
| 2,146,894 A | 2/1939 | Hickman |
| 2,180,356 A | 11/1939 | Hickman |
| 2,349,269 A | 5/1944 | Hickman |
| 2,985,589 A | 5/1961 | Broughton et al. |
| 3,082,228 A | 3/1963 | Sutherland |
| 3,158,541 A | 11/1964 | Sutherland |
| 3,696,107 A | 10/1972 | Neuzil |
| 3,706,812 A | 12/1972 | de Rosset et al. |
| 3,761,533 A | 9/1973 | Otani et al. |
| 4,061,556 A | 12/1977 | Reis et al. |
| 4,124,528 A | 11/1978 | Modell |
| 4,147,624 A | 4/1979 | Modell |
| 4,156,688 A | 5/1979 | Zosel |
| 4,352,746 A | 10/1982 | Bracco et al. |
| 4,377,525 A | 3/1983 | D'Alelio et al. |
| 4,377,526 A | 3/1983 | Fujita et al. |
| 4,415,554 A | 11/1983 | Horrobin |
| 4,526,902 A | 7/1985 | Rubin |
| 4,554,107 A | 11/1985 | Takao |
| 4,564,475 A | 1/1986 | Masaichiro |
| 4,615,839 A | 10/1986 | Seto et al. |
| 4,623,488 A | 11/1986 | Takao |
| 4,675,132 A | 6/1987 | Stout et al. |
| 4,681,896 A | 7/1987 | Horrobin |
| 4,692,280 A | 9/1987 | Spinelli et al. |
| 4,758,592 A | 7/1988 | Horrobin et al. |
| 4,764,392 A | 8/1988 | Yasufuku et al. |
| 4,792,418 A | 12/1988 | Rubin et al. |
| 4,804,555 A | 2/1989 | Marschner et al. |
| 4,956,286 A | 9/1990 | Macrae |
| 4,956,287 A | 9/1990 | Suzuki et al. |
| 4,996,072 A | 2/1991 | Marschner et al. |
| 5,013,443 A | 5/1991 | Higashidate et al. |
| 5,091,117 A | 2/1992 | Athnasios et al. |
| 5,106,542 A | 4/1992 | Traitler et al. |
| 5,130,061 A | 7/1992 | Cornieri et al. |
| 5,130,449 A | 7/1992 | Lagarde et al. |
| 5,211,812 A | 5/1993 | Vielberth et al. |
| 5,243,046 A | 9/1993 | Traitler et al. |
| 5,316,927 A | 5/1994 | Zaks et al. |
| 5,340,602 A | 8/1994 | Hoche |
| 5,374,751 A | 12/1994 | Cheng et al. |
| 5,436,018 A | 7/1995 | Massie et al. |
| 5,480,787 A | 1/1996 | Negishi et al. |
| 5,502,077 A | 3/1996 | Breivik et al. |
| 5,558,893 A | 9/1996 | Muraldihara |
| 5,656,667 A | 8/1997 | Breivik et al. |
| 5,698,594 A | 12/1997 | Breivik et al. |
| 5,719,302 A | 2/1998 | Perrut et al. |

(Continued)

FOREIGN PATENT DOCUMENTS

AT 328597 3/1976

(Continued)

OTHER PUBLICATIONS

Julshamn et al. "Fiskeridirektoratets skrifter serie teknologiske undersokelser", vol. 5, No. 15, 1978.*

(Continued)

Primary Examiner—Deborah D Carr
(74) Attorney, Agent, or Firm—Finnegan, Henderson, Farabow, Garrett & Dunner, L.L.P.

(57) ABSTRACT

The invention relates to a process for decreasing the amount of environmental pollutants in a mixture comprising a fat or an oil, being edible or for use in cosmetics, the fat or oil containing the environmental pollutants, which process comprises the steps of adding a volatile working fluid to the mixture, where the volatile working fluid comprises at least one of a fatty acid ester, a fatty acid amid, a free fatty acid and a hydro-carbon, and subjecting the mixture with the added volatile working fluid to at least one stripping processing step, in which an amount of environmental pollutant present in the fat or oil, being edible or for use in cosmetics, is separated from the mixture together with the volatile working fluid. The present invention also relates to a volatile environmental pollutants decreasing working fluid, for use in decreasing an amount of environmental pollutants present in a fat or oil, being edible or for use in cosmetics. In addition, the present invention relates to a health supplement, a pharmaceutical and an animal feed product prepared according to the process mentioned above.

21 Claims, 2 Drawing Sheets

U.S. PATENT DOCUMENTS

| | | | |
|---|---|---|---|
| 5,792,795 | A | 8/1998 | Buser et al. |
| 5,945,318 | A | 8/1999 | Breivik et al. |
| 5,948,818 | A | 9/1999 | Buser et al. |
| 6,204,401 | B1 | 3/2001 | Perrut et al. |
| 6,277,405 | B1 | 8/2001 | Stamm et al. |
| 6,518,049 | B1 | 2/2003 | Haraldsson et al. |
| 2002/0077361 | A1 | 6/2002 | Peet et al. |
| 2003/0077342 | A1 | 4/2003 | Maffetone |
| 2003/0212138 | A1 | 11/2003 | Obukowicz |
| 2004/0210070 | A1 | 10/2004 | Kruidenberg |
| 2005/0171200 | A1 | 8/2005 | Calder et al. |
| 2006/0134303 | A1 | 6/2006 | Sondbo et al. |
| 2006/0148047 | A1 | 7/2006 | Haraldsson et al. |
| 2006/0166935 | A1 | 7/2006 | Bryhn |
| 2006/0211762 | A1 | 9/2006 | Rongen et al. |
| 2007/0036862 | A1 | 2/2007 | Rongen et al. |
| 2009/0118524 | A1 | 5/2009 | Albers et al. |

FOREIGN PATENT DOCUMENTS

| | | |
|---|---|---|
| AT | 347551 | 1/1979 |
| CA | 2260397 | 7/2000 |
| CL | 42559 | 10/1998 |
| CN | 1143384 A | 2/1997 |
| DE | 2 332 038 C3 | 1/1974 |
| DE | 3 839 017 A1 | 5/1990 |
| DE | 40 08 066 A1 | 8/1991 |
| DE | 100 24 420 A1 | 11/2001 |
| DE | 10 2006 012 866 A1 | 4/2007 |
| EP | 0 175 468 A2 | 3/1986 |
| EP | 0 189 610 A1 | 8/1986 |
| EP | 0 283 140 B1 | 9/1988 |
| EP | 0 292 846 B1 | 11/1988 |
| EP | 0 255 824 B1 | 1/1990 |
| EP | 0 442 184 A1 | 8/1991 |
| EP | 0 632 267 | 1/1995 |
| EP | 1 419 780 A1 | 5/2004 |
| FR | 2 103 302 | 4/1972 |
| FR | 2 527 934 | 12/1983 |
| FR | 2 651 148 A1 | 3/1991 |
| FR | 2 651 149 A1 | 3/1991 |
| FR | 2 686 028 A1 | 7/1993 |
| FR | 2 690 630 A1 | 11/1993 |
| FR | 2 694 208 A1 | 2/1994 |
| GB | 476134 | 12/1937 |
| GB | 485614 | 5/1938 |
| GB | 490433 | 8/1938 |
| GB | 493948 | 10/1938 |
| GB | 2 033 745 A | 5/1980 |
| GB | 1 604 554 | 12/1981 |
| GB | 2 148 713 A | 6/1985 |
| GB | 2 197 199 A | 5/1988 |
| GB | 2 218 984 A | 11/1989 |
| GB | 2 221 843 A | 2/1990 |
| JP | 59-14793 | 1/1984 |
| JP | 60-33088 | 2/1985 |
| JP | 61-192797 | 8/1986 |
| JP | 1-252294 | 10/1989 |
| JP | 2-25447 | 1/1990 |
| JP | 6-116585 | 4/1994 |
| JP | 6-293895 | 10/1994 |
| JP | 9-510091 | 10/1997 |
| JP | 39-05538 | 7/2003 |
| WO | WO 86/03781 | 7/1986 |
| WO | WO 87/02247 A1 | 4/1987 |
| WO | WO 87/03899 A1 | 7/1987 |
| WO | WO 88/08444 A1 | 11/1988 |
| WO | WO 89/11521 A1 | 11/1989 |
| WO | WO 90/12509 | 11/1990 |
| WO | WO 90/13656 | 11/1990 |
| WO | WO 91/16443 | 10/1991 |
| WO | WO 9524459 * | 4/1995 |
| WO | WO 95/24459 A1 | 9/1995 |
| WO | WO 98/18952 A1 | 5/1998 |
| WO | WO 00/73254 A1 | 12/2000 |
| WO | WO 2001/003810 A2 | 1/2001 |
| WO | WO 2007/107260 A1 | 9/2007 |

OTHER PUBLICATIONS

Abbate, R. et al. "n-3 PUFA supplementation, monocyte PCA expression and interleukin-6 production," *Prostaglandins, Leukotrienes and Essential Fatty Acids* (1996), 54(6), 439-444.

Abe, Y. et al. "Soluble Cell Adhesion Molecules in Hypertriglyceridemia and Potential Significance on Monocyte Adhesion," *Arteriosclerosis, Thrombosis, and Vascular Biology* (1998), 18(5), 723-731.

Abhyankar, B. "Further reduction in mortality following myocardial infarction," *J. Hospital Medicine* (2002), 63(10), 610-614.

Ackman, R.G. "Oils and Fats Group International Lecture: The year of the fish oils," *Chemistry and Industry* (1988) 139-145.

Adachi, S. et al. "Acidolysis of Sardine Oil by Lipase to Concentrate Eicosapentaenoic and Docosahexaenoic Acids in Glycerides," *J. Ferment. Bioeng.* (1993), 75(4), 259-264.

Bimbo, A. P. "Processing of Fish Oils" in *Fish Oils in Nutrition*, M.E. Stansby, Ed. (1990) 181-225.

Bimbo, A. P. "Guidelines for characterizing food-grade fish oil," *Inform* (1998), 9(5), 473-483.

Blonk, "Dose-response effects of fish-oil supplementation in healthy volunteers," *Am. J. Clin. Nutr.* (1990), 52, 120-127.

Bønaa, K. H. et al. "Effect of Eicosapentaenoic and Docosahexaenoic Acids on Blood Pressure in Hypertension," *New England J. of Medicine* (1990), 322, 795-801.

Bousquet, O. et al. "Counter-current chromatographic separation of polyunsaturated fatty acids," *J. Chromatography A* (1995), 704, 211-216.

Braunwald et al. "Harrison's Principles of Medicine," 11th ed. (McGraw-Hill, New York, 1985) p. 1204.

Breivik, H. et al. "Preparation of Highly Purified Concentrates of Eicosapentaenoic Acid and Docosahexaenoic Acid," *J. Am. Oil. Chem. Soc.* (1997), 74(11), 1425-1429.

Breivik, H. "Production and Quality Control of n-3 Fatty Acids," *Clinical Pharmacology* (1992), 5, 25-39.

Bryhn, M. et al. "The bioavailability and pharmacodynamics of different concentrations of omega-3 acid ethyl esters," *Prostaglandins, leukotrienes and Essential Fatty Acids* (2006), 75, 19-24.

CAPLUS English Abstract for De Bernardi et al. *Acta Toxicol. Ther.* (1987), 8(3), 339-352; Accession No. 1988:604885.

Calabresi, L. et al. "Omacor in familial combined hyperlipidemia : Effects on lipids and low density lipoprotein subclasses," *Atherosclerosis* (2000), 148(2), 387-396.

Chan, D. C. et al "Regulatory Effects of HMG CoA Reductase Inhibitor and Fish Oils on Apolipoprotein B-100 Kinetics in Insulin-Resistant Obese Male Subjects With Dyslipidemia," *Diabetes* (2002), 51, 2377-2386.

Cmolík, J. et al. "Physical refining of edible oils," (2000), 102, 472-486.

Cvengros, J. "Physical Refining of Edible Oils," *J. Am. Oil Chem. Soc.* (1995), 72(10), 1193-1196.

Database WPI: Week 199022, Derwent Publications Ltd., DE 3839017, 1990.

Database WPI: Week 198001, Derwent Publications Ltd., DE 2332038, 1974.

Database WPI: Week 197402, Derwent Publications Ltd., DE 2332038, 1974.

Database WPI: Week 199346, Derwent Publications Ltd., FR 2694208, 1994.

Database WPI: Week 199329, Derwent Publications Ltd., FR 2686028, 1993.

Database WPI: Week 199110, Derwent Publications Ltd., FR 2651148, 1991.

Database WPI: Week 199110, Derwent Publications Ltd., FR 2651149, 1991.

Database WPI: Week 198403, Derwent Publications Ltd., FR 2527934, 1983.
Database WPI: Week 197228, Derwent Publications Ltd., FR 2103302, 1972.
Database WPI: Week 198514, Derwent Publications Ltd., JP 60033088, 1985.
Database WPI: Week 198641, Derwent Publications Ltd., JP 61192797, 1986.
Database WPI: Week 198410, Derwent Publications Ltd., JP 59014793, 1984.
Database WPI: Week 198946, Derwent Publications Ltd., JP 1252294, 1989.
Database WPI: Week 200417, Derwent Publications Ltd., JP 3905538, 2007.
Database WPI: Week 199542, Derwent Publications Ltd., JP 9510091, 1997.
Database WPI: Week 199502, Derwent Publications Ltd., JP 6-293895, 1994.
Database WPI: Week 199421, Derwent Publications Ltd., JP 6116585, 1994.
Database WPI: Week 199010, Derwent Publications Ltd., JP 2025447, 1990.
De Bernardi et al. "Study of Perinatal and Postnatal Effects in Rats After Oral Administration with a New Drug Containing Eicosapentaenoic Acid and Docosahexaenoic Acid at 85%," *Acta Toxicol. Ther.* (1987), 8(3), 339-352.
Derwent abstract of ZA 198905758, 1990.
Diep, Q. N. et al "Docosahexaenoic Acid, a Peroxisome Proliferator-Activated Receptor-a Ligand, Induces Apoptosis in Vascular Smooth Muscle Cells by Stimulation of p38 Mitogen-Activated Protein Kinase," *Hypertension* (2000), 36, 851-855.
Donadio, J. V. "Use of fish oil to treat patients with immunoglobulin A nephropathy" *Am. J. Clin. Nutr.* (2000), 71(Suppl), 373S-375S.
Donadio, J. V. et al. "A Randomized Trial of High-Dose Compared with Low-Dose Omega-3 Fatty Acids in Severe IgA Nephropathy," *J. Am. Soc. Nephrol.* (2001), 12(4), 791-799.
Durrington, P. N. et al. "An omega-3 polyunsaturated fatty acid concentrate administered for one year decreased triglycerides in simvastatin treated patients with coronary heart disease and persisting hypertriglyceridaemia," *Heart* (2001), 85(5), 544-548.
English translation of AT 328597, 1976.
English translation of CL 42559, 1998.
EPAX marketing information (7 pages), 1987.
EPAX production information (6 pages), 1987.
Franzosi, M. G. et al "Cost-Effectiveness Analysis of n-3 Polyunsaturated Fatty Acids (PUFA) after Myocardial Infarction," *Pharmacoeconomics* (2001), 19(4), 411-420.
Gauglitz, E.J. et al. "Adsorptive Bleaching and Molecular Distillation of Menhaden Oil," *Journal of the American Oil Chemists Society* (1965), 42, 561-563.
Gissi-Prevenzione Investigators "Dietary supplementation with n-3 polyunsaturated fatty acids and vitamin E after myocardial infarction: results of the GISSI-Prevenzione trial," *Lancet* (1999), 354, 447-455.
Hamazaki, T. et al. "Effects of fish oil rich in eicosapentaenoic acid on serum lipid in hyperlipidemic hemodialysis patients," *Kidney International* (1984), 26(1), 81-84.
Haraldsson, G. G. et al. "Studies on the Positional Specificity of Lipase from *Mucor miehei* During Interesterifcation Reactions of Cod Liver Oil with n-3 Polyunsaturated Fatty Acid and Ethyl Ester Concentrations," *Acta Chemica Scandinavica* (1991), 45, 723-730.
Haraldsson, G. G. et al. "Separation of Eicosapentaenoic Acid and Docosahexaenoic Acid in Fish Oil by Kinetic Resolution Using Lipase," *J. Am. Oil Chem. Soc.* (1998), 75(11), 1551-1556.
Haraldsson, G. G. et al. "The Preparation of Concentrates of Eicosapentaenoic Acid an Docosahexaenoic Acids by Lipase-Catalyzed Transesterification of Fish Oil with Ethanol," *J. Am. Oil. Chem. Soc.* (1997), 74(11), 1419-1424.
Harris, W. S. et al. "Safety and efficacy of Omacor in sever hypertriglyceridemia," *Journal of Cardiovascular Risk* (1997), 4(5-6), 385-391.

Hellström, "Some Foreign Recommendations on the Treatment of Hyper-lipidaemias," in *Treatment of Hyperlipidemia*, National Board of Health and Welfare Drug Information Center, Sweden (1989) 131-137.
Hellström "Treatment of Hyperlipidemia: Opinions and recommendations from the group," in *Treatment of Hyperlipidemia*, National Board of Health and Welfare Drug Information Committee, Sweden (1989) 147-158.
Hogg, R. J. et al. "Advances in Treatment: Immunoglobulin A Nephropathy," *Seminars in Nephrology* (1996), 16(6) 511-516.
Hoshino, T. et al. "Selective Hydrolysis of Fish Oil By Lipase to concentrate N-3 Polyunsaturated Fatty Acids," *Agric. Biol. Chem.* (1990), 54(6), 1459-1467.
Information from http://www.epax.com (6 pages), 2004.
Information from http://www.omacor.com (25 pages), 2004.
Information from http://www.omacorrx.com (45 pages), 2004.
Japanese Litigation, Demand for Trial dated Aug. 31, 2007.
Johansen, O. et al. "n-3 Fatty Acids Do Not Prevent Restenosis After Coronary Angioplasty: Results from the Cart Study," *Journal of the American College of Cardiology* (1999), 33(6), 1619-1626.
Julshamn, K. et al. "Removal of DDT and its metabolites from fish oils by molecular distillation," *Fiskeridirektoratets Skrifter Serie Teknologiske Undersøkelser* (1978), 5(15), 3-11.
Kanematsu et al "Studies on the behaviour of trace components in oils and fats during processing for edible use. I. Removal of organochlorine pesticides and polychlorinated biphenyls (PCB) from oils and fats," *J. of Japan. Oil Chemists' Society* (1976), 25(1), 38-41.
Kinsella et al. *Seafoods and Fish Oils in Human Health and Disease* (New York, Marcel Dekka Inc. 1987) pp. 7-9.
Kris-Etherton et al. "Fish Consumption, Fish Oil, Omega-3 Fatty Acids, and Cardiovascular Disease," *Circulation* (2002), 106, 2747-2757.
Kuk, M. S. "Supercritical carbon dioxide extraction of cottonseed with co-solvents," *J. Am. Oil Chem. Soc.* (1994), 71(12), 1353-1356.
Larsen et al. "Biosynthesis of Alginate," *Int. Seaweed Symp.* $7^{th}$ (1971), 491-495.
Lie, E. et al. "Esterification of polyunsaturated fatty acids with lipases from different sources," *International J. of Food Science and Technology* (1992), 27, 73-76.
Lie, et al. "Fatty Acid Specificity of *Candida cylindracea* Lipase," *Feet, Seifen, Anstrichmittel* (1986), 88(9), 365-367.
Lim, G. P. et al. "A Diet Enriched with the Omega-3 Fatty Acid Docosahexaenoic Acid Reduces Amyloid Burden in an Aged Alzheimer Mouse Model," *J. Neuroscience* (2005), 25(12), 3032-3040.
Lovaza™ labeling information, Reliant Pharmaceuticals (revised Jun. 2007, 2 pages).
Lovaza™ marketing information (2 pages), 2007.
Luley, C. et al. "Bioavailability of Omega-3 Fatty Acids: Ethylester Preparation are Suitable as Triglyceride Preparations," *Nutrition Lances* (1990), 123-125.
Lungershausen, Y. K. et al. "Reduction of blood pressure and plasma triglycerides by omega-3 fatty acids in treated hypertensives," *Journal of Hypertension* (1994), 12(9), 1041-1045.
Marchioli, R. et al "Early Protection Against Sudden Death by n-3 Polyunsaturated Fatty Acids After Myocardial Infarction," *Circulation* (2002), 105, 1897-1903.
McNeill, G. P. "Lipase-Catalyzed Enrichment of Long-Chain Polyunsaturated Fatty Acids," *JAOCS* (1996), 73(11), 1403-1407.
Merck Index, $11^{th}$ Ed. (Rahway, NJ. Merck and Co., 1989) p. 925.
Moore, S. R. et al. "Production of Triglycerides Enriched in Long-Chain n-3 Polyunsaturated Fatty Acids from Fish Oil," *JAOCS* (1996), 73(11), 1409-1414.
Nicoud et al. *Proceedings of the $9^{th}$ International Symposium on Preparative and Industrial Chromatography*, Société Française de Chimie Apr. 1992, pp. 205-220.
Nilsson, W. B. "Supercritical fluid carbon dioxide fractionation of fish oil esters," *Adv. Seafood Chiochem., Pap. Am. Chem. Soc. Annu. Meet.* (1992), Meeting Date 1987, 151-168.
Nordøy, A. "Statins and omega-3 fatty acids in the treatment of dyslipidemia and coronary heart disease," *Minerva medica* (2002), 93(5), 357-363.

Omacor prescribing information from the FDA website: www.fda.gov/cder/foi/label/2004/21654lbl.pdf (9 pages), 2004.
Omacor prescribing information (1 page), 2004.
Omega-3-Acid Ethyl Esters 90, *European Pharmacopoeia* 5.3 (2006) 3571-3573.
Omega-3-Acid Ethyl Esters 60, *European Pharmacopoeia* 5.4 (2005) 3992-3997.
Perry, R.H. et al., *Chemical Engineers Handbook*, 5th Edition, McGraw-Hill, New York, 1973, 13-55 and 13-56.
Pownall, H. J. et al. "Correlation of serum triglyceride and its reduction by ω-3 fatty acids with lipid transfer activity and the neutral lipid compositions of high-density and low-density lipoproteins," *Atherosclerosis* (1999), 143(2), 285-297.
Proceedings From the Oct. 1987 Fish Oil Seminar, "Rendering Profits," (Alaska Fisheries Development Foundation, Inc. 1987) pp. 1-103.
Product specifications for EPAX 1050TG, 2006.
Product specifications for EPAX 4020EE, 2006.
Product specifications for EPAX 4020TG, 2006.
Product specifications for EPAX 4510TG, 2006.
Product specifications for EPAX 5500EE, 2006.
Product specifications for EPAX 6000EE, 2006.
Product specifications for EPAX 6000TG, 2006.
Product specifications for EPAX 6015EE, 2006.
Product specifications for EPAX 6015TG, 2006.
Reis, G. J. et al. "Effects of Two Types of Fish Oil Supplements on Serum Lipids and Plasma Phospholipid Fatty Acids in Coronary Artery Disease," *Am. J. Cardiology* (1990), 66, 1171-1175.
Shibata, T. et al. "Effects of peroxisome proliferator-activated receptor-a and -g agonist, JTT-501, on diabetic complications in Zucker diabetic fatty rats," *British J. of Pharmocol.* (2000), 130, 495-504.
Shimada, Y. et al. "Purification of Docosahexaenoic Acid by Selective Esterification of Fatty Acids from Tuna Oil with Rhizopus delemar Lipase," *JAOCS* (1997), 74(2), 97-101.
Stalenhoef, A. F. H. et al. "The effect of concentrated n-3 fatty acids versus gemfibrozil on plasma lipoproteins, low density lipoprotein heterogeneity and oxidizability in patients with hypertriglyceridemia," *Atherosclerosis* (2000), 153(1), 129-138.
Takagi, "Fractionation of Polyenoic Acids from Marine Lipids with Lipase," *Am. Oil Chem. Soc.* (1989), 66, 488-489.
Tanaka, Y. et al. "Preparative separation of acylglycerol by centrifugal partition chromatography (CPC). II. Concentration of EPA (eicosapentaenoic acid) and DHA (docosahexaenoic acid) from lipase-hydrolyzed fish oil" *Yukagaku* (1992), 41(4), 312-316.
Third Party Observation from corresponding European application No. 03764048.9-2108 dated Sep. 26, 2006.
Treybal, R.E., Mass-Transfer Operations, McGraw-Hill, New York, 1955, pp. 344-353.
Van Dam et al., "Efficacy of concentrated n-3 Fatty Acids in hypertriglyceridaemia—A Comparasion with Gemfibrozil:", Clin. Drug Invest., pp. 175-181, 2001.
Vericel, E. et al. "The influence of low intake of *n*-3 fatty acids on platelets in elderly people," *Atherosclerosis* (1999), 147(1), 187-192.
Xu, X. et al. "Purification and deodorization of structured lipids by short path distillation," *Eur. J. Lipid Sci. Technol.* (2002), 104, 745-755.
Young, W. "Processing of oils and fats," *Chemistry and Industry* (1978), 16, 692-703.
Zinger et al. CA 106:118610 (1986).
Zuyi, et al. "Stability of Microbial Lipase in Alcoholysis of Fish Oil During Repeated Enzyme Use," *Biotechnol. Lett.* (1993), 15(4), 393-398.
Zuyi, et al. "Lipase-catalyzed alcoholysis to concentrate the *n*-3 polyunsaturated fatty acid of cod liver oil," *Enzyme Microb. Technol.* (1993), 15, 601-606.
Ackman, R.G. et al., "The "basic" fatty acid composition of Atlantic fish oils: Potential similarities useful for enrichment of polyunsaturated fatty acids by urea complexation," *J. Am. Oil. Chem. Soc.* (1988) vol. 65, pp. 136-138.
Azhgikhin, I.S. et al., "Obtainment of an esters concentrate of the eicosapentaenoic and docosapentaenoic as a possible substitute of arachiden and Itenol," Pansovietic Institute, Moscow, dated Mar. 14, 1978.

Bang, H.O. et al., "Plasma lipid and lipoprotein pattern in Greenlandic West-coast Eskimos," *Lancet* (1971) vol. 1, pp. 1143-1145.
Bronsgeest-Schoute, H.C. et al., "The effect of various intakes of ω3 fatty acids on the blood lipid composition in healthy human subjects," *Am. J. Clin. Nutr.* (1981) vol. 34, pp. 1752-1757.
Connor, W.E., "Effects of omega-3 fatty acids in hypertriglyceridemic states," *Seminars in Thrombosis and Hemostasis* (1988) vol. 14, pp. 271-284.
Database WPI: Week 199010, Derwent Publications Ltd., JP 2025447.
Database WPI Week 200206, Derwent Publications Ltd., DE 100 24 420 A1.
EPAX product information (6 pages).
Eritsland, J. et al., "Effects of highly concentrated omega-3 polyunsaturated fatty acids and acetylsalicylic acid, alone and combined, on bleeding time and serum lipid profile," J. Oslo City Hosp. (1989), vol. 39, pp. 97-101.
Eritsland, J. et al., "The effect of Omacor™ in patients with hypertriglyceridaemia having undergone coronary artery bypass grafting," Final Report, Pronova Biocare, 1994.
"Fish oil, rich in omega-3-acids," European Pharmacopoeia 5.0 (2004) pp. 1595-1598.
Harris, W.S. et al., "The comparative reductions of the plasma lipids and lipoproteins by dietary polysaturated fats: Salmon oil versus vegetable oils," *Metabolism* (1983), vol. 32, pp. 179-184.
Hirai, A. et al., "Effect of oral administration of highly purified eicosapentaenoic acid and docosahexaenoic acid on platelet function and serum lipids in hyperlipidemic patients," *Adv. Prostag. Thromb. L.* (1989) vol. 19, pp. 627-631.
Holub et al., "Alterations in molecular species of cholesterol esters formed via plasma lecithin - cholesterol acyltransferase in human subjects consuming fish oil," Atherosclerosis (1987) vol. 66, pp. 11-18.
Joseph, J., Ed. "Biomedical Test Materials Program: Production Methods and Safety Manual," NOAA Technical Memorandum NMFS-SEFC-234, pp. 1-3, Oct. 1989.
Kantha, S.S., "Dietary effects of fish oils on human health: A review of recent studies," *Yale J. Biol. Med.* (1987) vol. 60, pp. 37-44.
Kobatake, Y. et al., "Dietary effect of w-3 type polyunsaturated fatty acids on serum and liver lipid levels in rats," *J. Nutr. Sci. Vitaminol.* (1983) vol. 29, pp. 11-21.
Kobatake, Y. et al., "Differential effects of dietary eicosapentaenoic and docosahexaenoic fatty acids on lowering of triglyceride and cholesterol levels in the serum of rats on hypercholesterolemic diet," *J. Nutr. Sci. Vitaminot* (1984) vol. 30, pp. 357-372.
Larsen, L.N. et al., "Heneicosapentaenoate (21:5n-3): Its incorporation into lipids and its effects on arachidonic acid and eicosanoid synthesis," *Lipids* (1997) vol. 32, pp. 707-714.
Leaf, A. et al., "Cariovascular effects of n-3 fatty acids," *New Eng. J. Med.* (1988) vol. 318, pp. 549-557.
Lovaza™ marketing information (2 pages).
Maxepa® product information (3 pages).
Medline Plus, "Triglycerides," U.S. National Library of Medicine and National Institutes of Health, 2008.
Mehta, J.T. et al., "Dietary supplementation with omega-3 polyunsaturated fatty acids in patients with stable coronary heart disease," *Am. J. Med.* (1988) vol. 84, pp. 45-52.
Morisaki, N. et al., "In vivo effects of cis-5,8,11,14,17-20:5 (n-3) and cis-4,7,10,13,16,19-22:6(n-3) on serum lipoproteins, platelet aggregation, and lipid metabolism in the aorta of rats," *Tohoku J. Exp. Med.* (1983) vol. 141, pp. 397-405.
Mueller, B.A. et al., "Biological mechanisms and cardiovascular effects of omega-3 fatty acids," *Clin. Pharmacy* (1988) vol. 7, pp. 795-807.
Nestel, P.J. et al., "Suppression by diets rich in fish oil of very low density lipoprotein production in man," *J. Clin. Invest.* (1984) vol. 74, pp. 82-89.
Phillipson, B.E. et al., "Reduction of plasma lipids and lipoproteins in hyperlipidemic patients by dietary ω-3 fatty acids," *Am. J. Clin. Nutr.* (1981) vol. 34, p. 629.

Ratnayake, W.M.N. et al., "Preparation of omega-3 PUFA concentrates from fish oils via urea complexation," *Fat Sci. Technol.* (1988), vol. 90, pp. 381-386.

Rote Liste, Eicosapen information, 1987.

Sanders, T.A.B., "The importance of eicosapentaenoic and docosahexaenoic acids," Ch. 7, pp. 101-116, in *The Role of Fats in Human Nutrition*, F.B. Padley et al., Eds., Ellis Horwood Ltd., Chichester, England, 1985.

Sanders, T.A.B. et al., "A comparison of the influence on plasma lipids and platelet function of supplements of ω3 and ω6 polyunsaturated fatty acids," *Br. J. Nutr.* (1983) vol. 50, pp. 521-529.

Sanders, T.A.B. et al., "The influence of different types of ω3 polyunsaturated fatty acids on blood lipids and platelet function in healthy volunteers," *Clinical Science* (1983) vol. 64, pp. 91-99.

Saynor, R. et al., "The long-term effect of dietary supplementation with fish lipid concentrate on serum lipids, bleeding time, platelets and angina," *Atherosclerosis* (1984) vol. 50, pp. 3-10.

Simons, L.A. et al., "On the effects of dietary n-3 fatty acids (Maxepa) on plasma lipids and lipoproteins in patients with hyperlipidaemia," *Atherosclerosis* (1985) vol. 54, pp. 75-88.

Simopoulos, A.P., "Omega-3 fatty acids from fish and fish oils: Nutritional and health effects," *Epitheorese Klinikes Farmakologias Kai Farmakokinetikes, Int. Ed.* (1987) vol. 1, pp. 23-31.

Smith, P. et al., "Influence of highly concentrated n-3 fatty acids on serum lipids and hemostatic variables in survivors of myocardial infarction receiving either oral anticoagulants or matching placebo," *Thromb. Res.* (1989) vol. 53, pp. 467-474.

Swanson, D.R., "Fish oil, Raynaud's Syndrome, and undiscovered public knowledge," *Perspect. Biol Med.* (1986) vol. 30, pp. 7-18.

Turchetto, E. et al., "Protective role of vitamin E on essential fatty acids," *Acta Vitaminol. Enzymol.* (1982) vol. 4, pp. 267-277. Abstract.

Von Lossonczy, T.O. et al., "The effect of a fish diet on serum lipids in healthy human subjects," *Am. J. Clin. Nutr.* (1978) vol. 31, pp. 1340-1346.

Detwiler, S.B., Jr, "Supplement to Bibliography on Molecular or Short Path Distillation" Oil and Soap, (1940) pp. 241-243.

UNEP Chemicals Data Fact Sheet, UNEP Chemicals, Regional Reports of the Regionally Based Assessment of Persistent Toxic Substances Program (2002) (1 page).

Yaws Handbook of Antoine Coefficients for Vapour Pressure, $2^{nd}$ Electronic Edition, 2009 (extract, 6 pages).

\* cited by examiner

Figure 2
Removal of environmental pollutants in fish oil full scale

|  | IUPAC No | Enhet | Before stripping Conc. | TE (WHO) pg/g | After stripping Conc. | TE (WHO) pg/g |
|---|---|---|---|---|---|---|
| Dieldrin |  | ng/g | 60 |  | <3,20 |  |
| Sum Hexachlorocyclohexane |  | ng/g | 72,8 |  | <0,23 |  |
| Sum DDE,DDD,DDT |  | ng/g | 170 |  | 4,02 |  |
| Hexachlorobenzene |  | ng/g | 27,5 |  | 0,25 |  |
| Trichlorobiphenyls |  | ng/g | 12,0 |  | 0,14 |  |
| Tetrachlorobiphenyls |  | ng/g | 68,3 |  | 0,20 |  |
| Pentachlorobiphenyls |  | ng/g | 155 |  | 1,95 |  |
| Hexachlorobiphenyls |  | ng/g | 160 |  | 4,09 |  |
| Heptachlorobiphenyls |  | ng/g | 30,5 |  | 1,31 |  |
| Octachlorobiphenyl | 194 | ng/g | 0,78 |  | 0,07 |  |
| Nonachlorobiphenyl | 206 | ng/g | <0,01 |  | <0,01 |  |
| Decachlorobiphenyl | 209 | ng/g | 0,36 |  | <0,01 |  |
| Sum PCB |  | ng/g | 427 | 7,36 | 7,78 | 0,17 |
| Tetrachlorodibenzodioxins |  | pg/g | 0,86 |  | 0,12 |  |
| Pentachlorodibenzodioxins |  | pg/g | 0,29 |  | <0,1 |  |
| Hexachlorodibenzodioxins |  | pg/g | 1,29 |  | <0,6 |  |
| Heptachlorodibenzodioxins |  | pg/g | <0,4 |  | <0,4 |  |
| Octachlorodibenzodioxins |  | pg/g | 0,73 |  | 0,71 |  |
| Sum PCDD |  | pg/g | 3,49 | 1,30 | 0,83 | 0,26 |
| Tetrachlorodibenzofurans |  | pg/g | 19,2 |  | <0,1 |  |
| Pentachlorodibenzofurans |  | pg/g | 5,43 |  | 0,36 |  |
| Hexachlorodibenzofurans |  | pg/g | 3,30 |  | 0,46 |  |
| Heptachlorodibenzofurans |  | pg/g | <1,2 |  | <1,2 |  |
| Octachlorodibenzofurans |  | pg/g | <1,00 |  | <1,00 |  |
| Sum PCDF |  | pg/g | 29,6 | 3,35 | 1,82 | 0,2 |
| Sum PCDD/PCDF |  | pg/g | 33,1 | 4,65 | 2,65 | 0,46 |
| 3,3',4,4'-TetCB | 77 | pg/g | 287 |  | 2,12 |  |
| 3,4,4',5-TetCB | 81 | pg/g | 4,94 |  | 0,09 |  |
| 3,3',4,4',5-PenCB | 126 | pg/g | 222 |  | 0,83 |  |
| 3,3',4,4',5,5'-HexCB | 169 | pg/g | 35,9 |  | 0,22 |  |
| Sum TE-PCB |  | pg/g |  | 22,6 |  | 0,09 |
| 2,2'4,4'-TetBDE | 47 | ng/g | 12,2 |  | 0,58 |  |
| 2,2',4,4',5-PenBDE | 99 | ng/g | 0,3 |  | <0,17 |  |

# PROCESS FOR DECREASING ENVIRONMENTAL POLLUTANTS IN AN OIL OR A FAT

This is a continuation of U.S. Patent Application No. 10/517,812, which entered the national stage under §371 on Dec. 14, 2004, from the international application no. PCT/IB2003/002827, filed on Jul. 8, 2003, which claims the benefit of priority to Swedish Application No. 0202188-9, filed on Jul. 11,2002, all of which are incorporated herein by reference.

TECHNICAL FIELD OF THE INVENTION

This invention relates to a process for decreasing the amount of environmental pollutants in a mixture comprising a fat or an oil, being edible or for use in cosmetics. The present invention also relates to a volatile environmental pollutants decreasing working fluid. In addition, the present invention relates to a health supplement, a pharmaceutical, a cosmetic product and an animal feed product prepared according to the process mentioned above.

BACKGROUND OF THE INVENTION

DDT (2,2 bis-(p-chlorophenyl)-1,1,1-trichloroethane) and its degradation products are today found almost everywhere in the global environment. Numerous studies also report on the accumulation of often relatively high concentrations of environmental pollutants like PCB, dioxins and brominated flame retardants, and pesticides like toxaphenes and DDT and its metabolites in the deposit of e.g. marine organisms. The hazard of these compounds for both humans and animals have caused a growing concern about the content of toxic substances in food and food stuff. Consumption of dioxins above safe levels over a lifetime may result in an increased risk of cancer.

Food products that have no or reduced amounts of pollutants are gaining popularity as well as an increasing share of the market. Consequently, removal or reduction of pollutants in food products have the potential to substantially increase marketability and value.

The commercially important polyunsaturated fatty acids in marine oils, such as fish oil, are preferably EPA (eicosapentaenoic acid, C20:5n-3) and DHA (docosahex-aenoic acid, C22:6n-3). The full nomenclature of these acids according to the IUPAC system is: EPA all-cis-5,8,11,14,17-eicosapentaenoic acid, DHA all-cis-4,7,10,13,16,19-docosahexaenoic acid. For many purposes it is necessary that the marine oils should be refined in order to increase the content of EPA and/or DHA to suitable levels, or to reduce the concentrations of, or even eliminate, certain other substances which occur naturally in the raw oil.

The fatty acids EPA and DHA are also proving increasingly valuable in the pharmaceutical and food supplement industries in particular. It is also very important for fish oils and other temperature sensitive oils (e.g. oils that contain long chain polyunsaturated fatty acids) to keep the temperature in some of the processes as low as possible.

The demand for marine oils of high quality is increasing. This issue forces the fish oil industry to consider use of alternative refining techniques for fish oils with inferior quality, i.e. oils with high amounts of free fatty acids that make the oils less useful for nutritional purposes and make traditional alkaline refining more complicated and costly. If environmental pollutants can be successfully removed from such fish oils they are appropriate for use in the animal feed industry, e.g. in animal feed products.

From the literature it is known that molecular distillation, or short path distillation as the technique alternatively may be named, can be used to remove the pesticides DDT and its metabolites from fish oil (K. Julshamn, L. Karlsen and O. R. Braekkan, Removal of DDT and its metabolites from fish oils by molecular distillation, Fiskeridirektoratets skrifter; Serie teknologiske undersokelser, Vol. 5 No. 15 (1973)). A practical upper limit was 65% removal together with a loss of about 25% of vitamin A. In many industrial fish oil refining processes a removal of DDT up to 65% is not satisfactory.

Anthony P. Bimbo: Guidelines for characterization of food-grade fish oil. INFORM 9(5), 473-483 (1998), reported that vacuum stripping or thin-film distillation can be used to remove chlorinated hydrocarbons and free fatty acids from fats or oils. A disadvantage by using vacuum stripping to refine oils is that sufficient results only can be achieved then the vacuum stripping process is carried out at a high temperature. Further, the high temperature gives rise to undesirable side reactions.

Jiri Cmolik og Jan Pokorny: Physical refining of edible oils, Eur. J. Lipid Sci. Technol. 102(7), 472-486 (2000) describes physical refining of edible oils and the use of molecular distillation for removal of undesirable substances in crude oils, preferably crude vegetable oils, respectively the use of steam stripping in order to remove free fatty acids from an oil composition. Physical refining is used to refine oils of good quality, i.e. oils with small amounts of free fatty acids. However, physical refining is more complicated and costly for oils with inferior quality.

In WO 9524459 a process for treating an oil composition containing saturated and unsaturated fatty acids in the form of triglycerides, in order to obtain a refined product with higher concentrations of the polyunsaturated fatty acids, is presented. This process also is intended to be used for removal of some environmental pollutants from an oil composition, wherein the process comprises the steps of; subjecting the oil composition to a transesterification reaction and thereafter subjecting the product obtained in the first step to one or more molecular distillations. This technique has the severe limitation that it can only be used for fish oils that have been partially transesterified using a lipase catalyst that discriminates against omega-3 fatty acids. Obviously, this technique can not be used for commercial fish oils.

In EP0632267 A1 a method of measuring the content of polycyclic aromatic hydrocarbons(PAH) remaining in lanolin is presented. The European patent document also describes a method of removing PAH remaining in wool grease or lanolin by a vacuum distillation of the grease or lanolin under specified conditions either directly or after having been treated with a borate and, if necessary, obtaining various lanolin derivatives from the treated wool grease or lanolin. However, the technique described in said patent document requires very high temperatures (230° C.) in order to achieve 90% reduction in PAH content.

Another interesting observation is that the removal of environmental pollutants from fats or oils is not a trivial matter. Several different techniques, some of which are mentioned above, to accomplish this task have been developed, but none of them is sufficiently effective and gentle to the fat or oil. In addition, it is nowadays a problem for e.g. the marine oil industry that the amounts of pollutants in e.g. fish oil become increased.

SUMMARY OF THE INVENTION

One object of the present invention is to offer an effective process for decreasing the amount of environmental pollutants in a fat or an oil, being edible or for use in cosmetics.

According to a first aspect of the invention, this and other objects are achieved with a process for decreasing the amount of environmental pollutants in a mixture comprising a fat or an oil, being edible or for use in cosmetics, the fat or oil containing the environmental pollutants, which process comprises the steps of adding a volatile working fluid to the mixture, where the volatile working fluid comprises at least one of a fatty acid ester, a fatty acid amide, a free fatty acid and a hydrocarbon, and subjecting the mixture with the added volatile working fluid to at least one stripping processing step, in which an amount of environmental pollutants present in the fat or oil, being edible or for use in cosmetics, is separated from the mixture together with the volatile working fluid. Herein, "an amount" is interpreted to include decreasing of an amount up to 95-99% of some environmental pollutants, i.e. a substantial removal of specific pollutants and/or toxic components from a fat or oil composition.

The use of a volatile working fluid in a stripping process for decreasing an amount of environmental pollutants in a mixture comprising a fat or an oil, being edible or for use in cosmetics, containing the environmental pollutants, and/or toxic components, has a number of advantages.

An advantage of using a volatile working fluid in a process comprising at least one stripping processing step is that an amount of environmental pollutants in the mixture can more easily be stripped off together with the volatile working fluid, i.e. the environmental pollutants present in the fat or oil mixture is separated from the mixture together with the working fluid. Preferably this is possible as long as the volatile working fluid is essentially equally or less volatile than the environmental pollutants that is to be removed from the fat or oil mixture. The stripped pollutants (components) and most of the volatile working fluid will be found in the distillate.

In addition, the use of a volatile working fluid comprising at least one of a fatty acid ester, a fatty acid amide, a free fatty acid and a hydrocarbon in at least one stripping process step results in that use of the inventive process decreases the amount of dioxins in a fish oil with more than 95%. By using the inventive process it is also possible to decrease the amount of chlorinated organic pesticides (or pollutants) in a mixture comprising a fat or an oil, being edible or for use in cosmetics, which pollutants are even less volatile than DDT, for instance dioxines, toxaphenes and/or PCB.

Separation of such heavy and undesirable components from the fat or oil mixture according to the invention, using mild conditions that do not decompose even very unsaturated oils, is surprising. Further, according to the present stripping process it is possible to decrease an effective amount of PAH at much lower temperatures compared to the techniques known from the prior art.

Another advantage of adding a volatile working fluid to an oil or fat mixture prior to a stripping process is that removal of free fatty acids is facilitated, which will result in a higher quality of the oil product.

In addition, the volatile working fluid according to the invention allows environmental pollutants or other toxic components to be stripped off by e.g. molecular distillation even from oils of lower quality, i.e. oil for feed purposes. Further, the process according to the invention can also be used for decreasing the amount of toxic compounds in a ricinus oil, preferably trace of ricinine (1,2-dihydro-4-methoxy-1-methyl-2-oxo-3-pyridinecarbonitrile). By using the process according to the invention the amount of ricinine may be decreased with at least 80-90%.

In a preferred embodiment of the present invention the volatile working fluid is an organic solvent or solvent mixture or a composition with a suitable volatility.

The volatile working fluid of the present invention is at least one of a fatty acid ester, a fatty acid amide, a free fatty acid, bio-diesel and a hydrocarbon, also including any combinations thereof.

In another preferred embodiment the volatile working fluid comprises at least one fatty acid ester composed of C10-C22 fatty acids and C1-C4 alcohols, or a combination of two or more fatty acid ester each composed of C10-C22 fatty acids and C1-C4 alcohols. Preferably, the volatile working fluid is at least one of amides composed of C10-C22 fatty acids and C1-C4 amines, C10-C22 free fatty acids, and hydrocarbons with a total number of carbon atoms from 10 to 40. Most preferably, the volatile working fluid is a mixture of fatty acids from marine oils, e.g. fish body oil and/or fish liver oil, and/or ethyl or methyl esters of such marine fatty acids.

In another preferred embodiment of the process the volatile working fluid is constituted by free fatty acids comprised in the fat or oil, being edible or for use in cosmetics, containing the environmental pollutants, i.e. the fat or oil itself contains free fatty acids. Here, the free fatty acids in the oil or fat acts as the volatile working fluid. Further, free fatty acids in an oil or fat also can contribute to an additive effect in a stripping process by partially acting as an internal working fluid (or by being an active part of the working fluid) in the process. Such oils or fats mentioned above could e.g. be silage oils or oils that have been stored or transported for a long period of time. This means that a volatile working fluid can be added to an oil or fat mixture prior to a stripping process and/or being comprised in the fat or oil mixture containing the environmental pollutants or toxic components. In this way, the invention surprisingly is very efficient for purifying oils that normally are classified as oils of low quality.

In another preferred embodiment of the stripping process, the volatile working fluid is constituted by free fatty acids comprised in a mixture of at least a marine oil, e.g. a fish oil, with a high content of free fatty acids (a low quality marine oil), wherein the free fatty acids in the oil mixture acts as a working fluid.

Further, it is hereby possible to decrease the amount of environmental pollutants and to reduce the amount of free fatty acids in the marine oil at the same time and in the same process.

In another preferred embodiment of the process, the fatty acid esters, fatty acid amides and free fatty acids are obtained from at least one of vegetable, microbial and animal fat or oil. The fatty acid esters mentioned above can e.g. be a by-product from distillation of an ethyl ester mixture prepared by ethylation of preferably a fish oil. In the process industry trade with intermediates is increasing and opens up for an extra financial income.

In another preferred embodiment the volatile working fluid is obtained from at least one of animal fat or oil, wherein the animal fat or oil preferably is a marine oil e.g. a fish oil or an oil from other marine organism e.g. sea mammals.

Further, in another preferred embodiment of the invention the fat or oil, being edible or for use in cosmetics, is obtained from at least one of vegetable, microbial and animal fat or oil, or any combination thereof. Preferably, the fat or oil, being edible or for use in cosmetics, is a marine oil. Marine oils that have no or reduced amounts of environmental pollutants are gaining popularity as well as an increasing share of the market. Consequently, removal or reduction of pollutants in e.g. fish oils of high quality as well as fish oils with inferior quality have the potential to substantially increase marketability and value. Therefore, in a more preferred embodiment of the invention the marine oil is obtained from fish or sea mammals, containing at least saturated and unsaturated fatty acids in the form of triglycerides. It is important to note that the invention is not limited to procedures were the working fluid is prepared from the same origin as the oil that is being purified.

Additionally, the fat or oil, being edible or for use in cosmetics, may also be a ricinus oil for use in cosmetics or medicinal applications. It is also of commercial interest to decrease the amount of pollutants or toxic components in oil mixtures or blends comprising at least one microbial oil that e.g. will be used in food products or as food supplement (e.g. infant formula) preferable suitable for humans.

In another preferred embodiment of the invention the fat or oil, being edible or for use in cosmetics, is a tocopherol concentrate prepared from a condensate from at least one deodorization process of at least one vegetable oil, wherein the tocopherol concentrate containing at least one of PAH and volatile pollutants, or any combination thereof. Commercially available tocopherol concentrate contains about 65-90% tocopherol and it will be apparent for one skilled in the art that the stripping process according to the invention may be used to separate an amount of environmental pollutants from a tocopherol concentrate.

In a preferred embodiment of the invention, the ratio of (volatile working fluid):(fat or oil, being edible or for use in cosmetics) is about 1:100 to 15:100. In a more preferred embodiment the ratio of (volatile working fluid):(fat or oil, being edible or for use in cosmetics) is about 3:100 to 8:100.

In a preferred embodiment of the invention, said stripping process step is carried out at temperatures in the interval of 120-270° C.

In a most preferred embodiment, the stripping processing step is carried out at temperatures in the interval of 150-200° C. By adding a volatile working fluid to the fat or oil mixture at this temperatures the invention surprisingly shows that even termolabile polyunsaturated oils can be treated with good effect, without causing degradation of the quality of the oil.

In another preferred embodiment, the stripping processing step is carried out at a pressure below 1 mbar.

In another preferred embodiment, the stripping processing step is at least one of a thin-film evaporation process, a molecular distillation or a short-path distillation, or any combination thereof. If at least one stripping process step is a thin-film evaporation the process is also carried out at mixture flow rates in the range of 10-300 kg/h m$^2$, preferably 40-150 kg/h m$^2$. By using a stripping process, e.g. a distillation method, for decreasing the amount of environmental pollutants in a fat or oil mixture comprising a volatile working fluid it is possible to carry out the stripping processes at lower temperatures, which spare the oil and is at the same time favourable to the end oil product.

In a preferred embodiment of the invention, the volatile working fluid is stripped off together with the environmental pollutants by at least one short-path distillation or molecular distillation step. This is possible as long as the volatile working fluid is essentially equally or less volatile than the environmental pollutants that are to be separated from the fat or oil mixture.

In another preferred embodiment of the invention, the process allows the environmental pollutants to flash off most effective at process conditions of low temperatures and preferable high mixture flow rates. Further, this embodiment offers similar advantages as described above by using the volatile working fluid.

In a preferred embodiment according to the invention the stripping process is carried out by a molecular distillation in the following intervals; mixture flow rates in the interval of 10-300 kg/h·m$^2$, temperatures in the interval of 120-270° C. and a pressure below 1 mbar.

In a most preferred embodiment of the invention the molecular distillation is carried out at temperatures in the interval of 150-200° C. and at a pressure below 0.05 mbar.

In a further preferred process of the present invention, said process is a thin-film process that is carried out at 40-150 kg/h m$^2$ or at flow rates in the range of 400-1200 kg/h at a heated thin film area of 11 m$^2$; 36-109 kg/h·m$^2$. Please note, that the present invention can also be carried out in one or more subsequent stripping processing steps.

In another preferred embodiment of the present invention, for use in decreasing an amount of environmental pollutants and/or toxic components, such as dioxins and/or PCB, present in a fat or oil, being edible or for use in cosmetics, the working fluid is comprising at least one of a fatty acid ester, a fatty acid amide, a free fatty acid and a hydrocarbon with essentially equally or less volatility compared to the environmental pollutants that are to be separated from the fat or oil mixture, or any combination thereof.

Preferably, the volatile environmental pollutants decreasing working fluid is generated as a fractionation product. Additionally, the volatile environmental pollutants decreasing working fluid is a by-product, such as a distillation fraction, from a regular process for production of ethyl and/or methyl ester concentrates. This by-product according to the invention can be used in a new process for decreasing the amount of environmental pollutants in a fat or an oil. More preferably, the volatile environmental pollutants decreasing working fluid, for use in decreasing an amount of environmental and/or toxic components, present in a fat or oil, can be a by-product (a distillate fraction) from a regular process for production of ethyl ester concentrates, wherein a mixture comprising an edible or a non-edible fat or oil, preferably a fish oil, is subjected to an ethylating process and preferably a two-step molecular distillation. In the two-step molecular distillation process a mixture consisting of many fatty acids on ethyl ester form is separated from each other in; a volatile (light fraction), a heavy (residuum fraction) and a product fraction. The volatile fraction from the first distillation is distilled once more and the volatile fraction from the second distillation process is then at least composed of the volatile working fluid, preferably a fatty acid ethyl ester fraction. This fraction consists of at least one of C14 and C16 fatty acids and at least one of the C18 fatty acids from the fat or oil, and is therefore also compatible with the edible or non-edible oil. The fraction can be redistilled one or more times if that is deemed to be suitable. This prepared working fluid can then be used as a working fluid in a new process for decreasing the amount of environmental pollutants in a fat or an oil, wherein the edible or non-edible fats or oils and the oil or fat, being edible or for use in cosmetics, are of the same or different types.

In another embodiment of the invention a volatile working fluid may be produced by subjecting fats or oils from an available source, for instance fats or oils obtained from at least one of animal, microbial or vegetable origin, to an interesterification process, in which process the triglycerides in the fats or oils are converted into esters of aliphatic alcohols. Additionally, a bio-diesel and/or a mineral oil can be used as a volatile working fluid. In the case when the volatile working fluid is a biodiesel, it can be produced by a process, which is in common use for production of engine fuels (biodiesel), and therefore also known by a man skilled in the art, which process comprises mixing the fat or oil with a suitable amount of aliphatic alcohol, adding a suitable catalyst and heating the mixture for a period of time. Similar esters of aliphatic alcohols may also be produced by a high-temperature catalytic direct esterification process reacting a free fatty acid mixture with the appropriate aliphatic alcohol. The fatty acid ester mixture produced in this manner may be used as a volatile working fluid as it is, but normally the conversion to esters of aliphatic alcohols is not complete, the conversion process preferably leaving some un-reacted non-volatile glycerides in, the mixture. Additionally, some fats or oils may also contain certain amounts of non-volatile, non-glyceride components (e.g. polymers). Such non-volatile components will preferably be transferred to, and mixed with the final product, which product is low in environmental pollutants, when the fatty acid ester mixture is used as working fluid. A working fluid produced in this manner should therefore be subjected to a distillation, preferably a molecular and/or short path distillation, in at least one step, which distillation process generates a distillate more suitable to be used as a new volatile working fluid.

In another preferred embodiment of the invention the volatile working fluid comprises at least one of an ester and/or an amide composed of shorter fatty acids and longer alcohols or amines, or any combination thereof.

In a preferred embodiment of the invention, the volatile environmental pollutants decreasing working fluid, for use in decreasing an amount of environmental pollutants present in a fat or oil, being edible or for use in cosmetics, is preferably a fatty acid ester (e.g. fatty acid ethyl ester or fatty acid methyl ester), a fatty acid amide or free fatty acids obtained from at least one of vegetable, microbial and animal origin, or any combination thereof. Preferably, said animal origin is fish or sea mammals, i.e. that the volatile fat or oil environmental pollutants decreasing working fluid is obtained from marine oils, e.g. from fish or from sea mammals. Further, in a preferred embodiment of the volatile environmental pollutants decreasing working fluid, said fat or oil is edible for humans and/or animals or for use in cosmetics.

In another embodiment of the invention, a volatile environmental decreasing working fluid according to the present invention, is used in a process for decreasing an amount of environmental pollutants, in a mixture comprising a fat or oil, being edible or for use in cosmetics, preferably a marine oil, containing the unwanted components, in which process the volatile working fluid is added to the mixture and then the mixture is subjected to at least one stripping processing step, preferably a thin-film evaporation process, a molecular distillation or a short-path distillation, or any combination thereof, and in which process an amount of toxic components present in the fat or oil, being edible or for use in cosmetics, is separated from the mixture together with the volatile working fluid.

In another preferred embodiment a health supplement, a pharmaceutical and/or an animal feed product containing at least fat or oil (end) products, e.g. oil ingredient of fish feed, with a decreased amount of environmental pollutants or toxic components, prepared according to at least one of the previously mentioned processes is disclosed. For the pharmaceutical and food supplement industries, marine oils have to be processed in order to increase the content of EPA and/or DHA to suitable levels and the removal or reduction of different kinds of pollutants have the potential to substantially increase marketability and value. Therefore, the present invention also discloses a health supplement and a pharmaceutical respectively, containing at least a marine oil, such as fish oil, which marine oil is prepared according to the previously mentioned process, in order to decrease the amount of environmental pollutants in the marine oil.

In another embodiment of the invention the pharmaceutical and/or health supplement is preferably intended for treating cardiovascular diseases (CVD) and inflammatory diseases, but they also have positive effects on other CVD risk factors such as the plasma lipid profile, hypertension and vascular inflammation. In more preferred embodiment of the invention the pharmaceutical and/or health supplement comprises at least one of EPA/DHA ethyl esters and is intended for a range of potential therapeutic applications including; treatment of hypertriglyceridaemia, secondary prevention of myocardial infarction, prevention of atherosclerosis, treatment of hypertension and/or kidney disease and to improve children's learning ability.

Further, the present invention also disclose a marine oil product, prepared according to at least one of the previously mentioned processes. Preferably, the marine oil product is based on fish oil or a fish oil composition.

In addition, there is a demand for marine oils of high quality. This issue forces the fish oil industry to consider alternative refining techniques. Further, by using one of the processes according to the invention it is now possible to simultaneously decrease the amount of environmental pollutants and/or to decrease the amount of free fatty acids in e.g. marine oils with inferior quality with a good result. Such oils are appropriate to be used in e.g. animal feed products. If the oil or fat is constituted by high amounts of free fatty acids, said free fatty acids may act as the volatile working fluid in the stripping process.

In another preferred embodiment of the invention, an animal feed product, containing at least a marine oil, which marine oil is prepared according to one of the processes presented before, in order to decrease the amount of environmental pollutants and/or the amount of free fatty acids in the marine oil. Preferably the animal feed product is a fish feed product.

For companies producing tocopherol preparations it is of commercial interest to refine their tocopherol concentrate from environmental pollutants, especially PAH's (polycyclic aromatic hydrocarbons). Tocopherol is produced from condensate from deodorization of soy and/or palm oil. Vegetable oils are deodorized preferably in the same way as fish oils, but at higher temperatures in order to distil off the tocopherols. Therefore, the condensate from the mentioned process also contains, except components causing bad taste and odour of the oil, high amounts of tocopherol. Further, this condensate is raw material in all tocopherol preparations that are so-called natural preparations.

In another preferred embodiment of the invention a tocopherol concentrate product, based on a tocopherol concentrate prepared from a condensate from a deodorization process of at least one vegetable fat or oil, such as palm oil or soy oil, which concentrate contains at least one of PAH and volatile pollutants, is prepared according to the stripping process of the present invention, in order to decrease the amount of environmental pollutants in the tocopherol concentrate. The process for decreasing the amount of environmental pollutants and/or PAH's in a tocopherol concentrate, comprises the steps of adding a volatile working fluid to a tocopherol concentrate and subjecting the concentrate, with the added volatile working fluid, to a stripping processing step, in which preferably PAH's are separated from the concentrate with the volatile working fluid. The volatile working fluid may be at least one of the working fluids mentioned before, or any combinations thereof, and said stripping process step is carried out at process conditions mentioned before. In a embodiment of the invention said stripping process step is carried out at a temperature in the interval of 120-180° C. and at a pressure below 1 mbar. The ratio of (volatile working fluid): (tocopherol concentrate) is preferably about 4:100 to 8:100.

For the cosmetic industry it is of commercial interest to refine ricinus oil from trace of toxic components.

It is valuable for this industry to market cosmetic products, such as lipstick, that are essentially free from toxic components, such as ricinine. Ricinus oil is a vegetable oil produced from the seeds of *Ricinus communis L., Euphorbiaceae*. The oil is a triglyceride of fatty acids, with ricinoleic acid (d-12-hydroxyoleic acid) as the major fatty acid (approximately 87%). Due to the hydroxyl group of ricinoleic acid, ricinus oil can not be refined in traditional ways, i.e. by alkali refining. Thus, traces of toxic components may not be easily removed.

Ricinine is a toxic nitrilpyridinone that might be present in the oil in trace amounts. Herein, the invention also disclose a cosmetic product, based on ricinus oil, which ricinus oil is prepared according to at least one of the processes mentioned before, in order to decrease the amount of toxic components in the ricinus oil.

In another preferred embodiment of the invention the fat or oil is a ricinus oil, for use in cosmetics or medicinal applications, and the pollutants that are to be separated according to the process of the invention are toxic compounds, such as nitrilpyridinones.

In a preferred embodiment, the process for decreasing the amount of toxic compounds in a ricinus oil, preferably trace of ricinine, comprises the steps of adding a volatile working fluid to a ricinus oil mixture and subjecting the mixture, with the added volatile working fluid, to a stripping processing step, in which preferably traces of ricinine (from the ricinus oil) is separated from the mixture with the volatile working fluid. The volatile working fluid may be at least one of the working fluids mentioned before, or any combinations thereof. In a more preferred process in order to decrease an amount of toxic compounds in a ricinus oil, the stripping processing step is at least one of a molecular distillation process, a thin-film evaporation process or a short-path distillation or any combination thereof, carried out at temperatures in the interval of 120-220° C., at a pressure below 0.1 mbar. In the case of a thin-film evaporation process the process is carried out at a mixture flow rate in the interval of 10-300 kg/h m².

In a most preferred embodiment of the invention, the ricinus oil mixture was distilled at a temperature about 170° C., a pressure around 0.001 mbar respectively a mixture flow rate about 150 kg/h-m². Up to 95% of the amount of ricinine present in the start oil may be removed with the stripping process according to the invention.

DEFINITIONS

As used herein the term environmental pollutants preferably means toxic components and/or pesticides like polychlorinated biphenyls (PCB), DDT and its metabolites, organic compounds found in the sea environment and identified as potentially harmful and/or toxic; Polychlorinated triphenyls (PCTs), dibenzo-dioxins (PCDDs), and dibenzo-furans (PCDFs), Chlorophenols and hexachloro-cyclohexanes (HCHs), toxaphenes, dioxins, brominated flame retardants, polyaromatic hydrocarbons (PAH), organic tin-compounds (e.g. tributyltin, triphenyltin) and organic mercury-compounds (e.g. Methyl-Mercury).

As used herein the term oil and fat means fatty acids in at least one of the triglyceride and phospholipid forms. Generally, if the start material in the stripping process is a marine oil, the oil may be any of raw or partially treated oil from fish or other marine sources and which contains fatty acids, including polyunsaturated fatty acids, in the form of triglycerides. Typically, each triglyceride molecule in such a marine oil will contain, more or less randomly, different fatty acid ester moieties, be the saturated, monounsaturated or polyunsaturated, or long chain or short chain. Further, examples of vegetable oils or fats are corn oil, palm oil, rapeseed oil, soybean oil, sunflower oil and olive oil.

Further, the fat or oil may be pre-processed in one or several steps before constituting the start material in the stripping process as described above. An example of such a pre-processing step is a deodorization process. It shall also be noted that the fat or oil may be edible in one or several such pre-processing steps and/or in the processing steps according to the invention.

As used herein the term edible means edible for humans and/or animals. Additionally, as used herein the term "for use in cosmetics" means an oil or a fat that can be used in products that contributes to enhance humans appearance and/or health, e.g. cosmetic and/or beauty care products.

As used herein the term working fluid is interpreted to include a solvent, a solvent mixture, a composition and a fraction, e.g. a fraction from a distillation process, that has a suitable volatility, comprising at least one of esters composed of C10-C22 fatty acids and C1-C4 alcohols, amides composed of C10-C22 fatty acids and C1-C4 amines, C10-C22 free fatty acids, mineral oil, hydrocarbons and bio-diesel.

As used herein the term essentially equally or less volatile is interpreted to include that the volatile working fluids having a suitable volatility in relation to the volatility of the environmental pollutants that is to be stripped off from a fat or oil mixture. Further, commonly this is the case when the volatility of the working fluid is the same or lower than the volatility of the environmental pollutants. However, the term essentially equally or less volatile is also intended to indude the case when the volatile working fluid is somewhat more volatile than the environmental pollutant.

Further, as used herein the term stripping is interpreted to include a general method for removing, separating, forcing or flashing off gaseous compounds from a liquid stream. In addition, the term "stripping processing step" preferable herein is related to a method/process for decreasing the amount of environmental pollutants in an oil or fat by one or more distilling or distillation processes, e.g. short path distillations, thin-film distillations (thin-film stripping or thin-film (steam) stripping), falling-film distillations and molecular distillations, and evaporation processes.

As used herein the term "oils with a low quality" preferably means that the oil contains high amounts of free fatty acids, that makes them less useful for nutritional purposes and that traditional alkaline refining in such oils is complicated and costly. Additionally, as used herein, the term mineral oil is interpreted to indude mineral oil products such as e.g. fractions from distillation processes and white spirit. As used herein hydrocarbons is interpreted to include organic compounds, that are relatively large molecules composed mainly of carbon and hydrogen. They can also include nuclei of nitrogen, phosphorus, sulphur, and chlorine, among others.

As used herein bio-diesel means a commercial product (or products under development) used as an environment friendly alternative to fuel for cars comprising e.g. methyl esters from preferable vegetable or animal oils.

As used herein the term marine oils includes oil from fish, shellfish (crustaceans) and sea mammals. Non limiting examples of fish oils are e.g. Menhaden oil, Cod Liver oil, Herring oil, Capelin oil, Sardine oil, Anchovy oil and Salmon oil. The fish oils mentioned above may be recovered from fish organs, e.g. cod liver oil, as well as from the meat of the fish or from the whole fish.

As used herein the term health supplement is interpreted to include food and food supplement to animals and/or humans, fortification of food, dietary supplement, functional (and medical) food and nutrient supplement.

As used herein the term "treating" means both treatment having a curving or alleviating purpose and treatment having a preventive purpose. The treatment can be made either acutely or chronically. Herein the term animal feed product means food or food supplement specially to animals e.g. fish, fowls, pigs and furred (fur-bearing) animal.

As used herein the term fish feed product also includes a fish larvae feed product.

As used herein the term microbial oils also includes "single cell oils" and blends, or mixtures, containing unmodified microbial oils. Microbial oils and single cell oils are those oils naturally produced by microorganisms during their lifespan.

Further, a fat or an oil, being edible or for use in cosmetics, according to the invention can also be a blend of e.g. microbial oils, fish oils, vegetable oils, or any combination thereof.

As used herein the term free fatty acids means fatty acids in free acid form. The free fatty acids is operative as a volatile working fluid and/or included in the fat or oil, being edible or for use in cosmetics.

As used herein the term "together with", means that the volatile working fluid will be stripped off together with, combined with, or adhering the pollutants, namely that the pollutants will accompany the working fluid.

As used herein the term acid value of a fat or an oil means the amount of free acids presented in a fat or an oil equal to the number of milligrams of potassium hydroxide needed to neutralize one gram of the oil, i.e. that the term serves as an index of the efficiency of refining. This means that a high acid value is characteristic for low quality oil or fat products.

While the invention has been described in detail and with reference to specific embodiments thereof, it will be apparent for one skilled in the art that various changes and modifications, i.e. other combinations of temperatures, pressures, and flow rates during the stripping process can be made therein without departing from the spirit and scope thereof.

BRIEF DESCRIPTION OF THE DRAWINGS

The advantages and details of the present invention will become apparent from the following description when taken in conjugation with the accompanying drawings, in which;

FIG. 2 shows the concentrations of different environmental pollutants in a fish oil mixture before and after stripping according to the present disclosure.

DETAILED DESCRIPTION OF PREFERRED EMBODIMENTS

Figure 1:
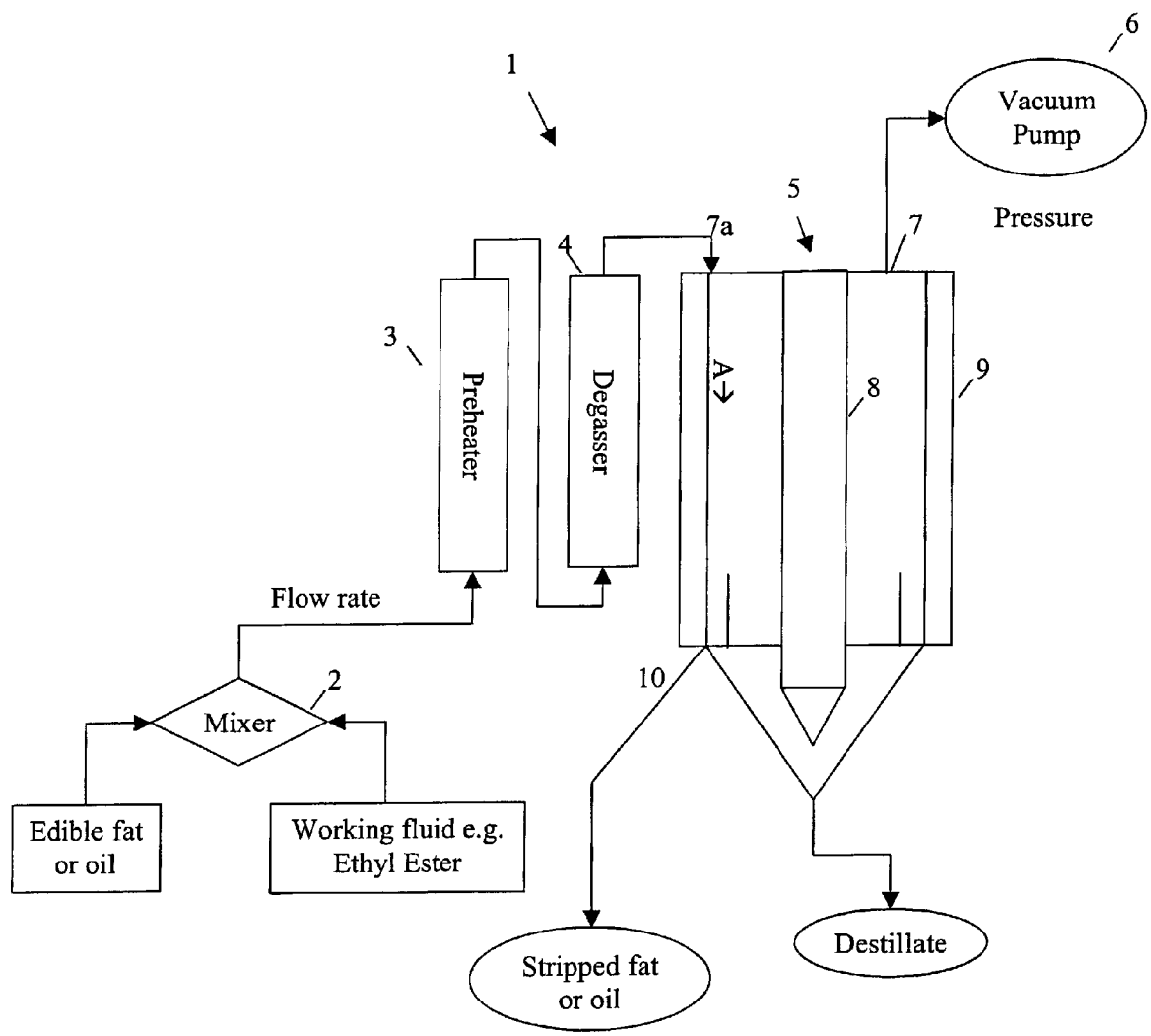
FIG. 1 is a schematic flow chart of one embodiment illustrating a method for decreasing the amount of environmental pollutants in a fat or an oil, being edible or for use in cosmetics, by adding a volatile working fluid prior to a molecular distillation.

A number of preferred embodiments of the process for decreasing the amount of environmental pollutants in a mixture comprising a volatile working fluid and a fat or an oil, being edible or for use in cosmetics, containing environmental pollutants will be disclosed below.

A first embodiment of a process for decreasing the amount of environmental pollutants in a fat or an oil, being edible or for use in cosmetics, by adding a volatile working fluid prior to a molecular distillation is presented in FIG. 1. The starting fat or oil, being edible or for use in cosmetics, in the first embodiment of the invention is a fish oil whether freshly refined, reverted or mixtures thereof characterized by a level of environmental pollutants. The exact amount of environmental pollutants varies depending upon such factors as fish species, seasonality, geographical catch location and the like.

As used herein the term molecular distillation is a distillation process performed at high vacuum and preferably low temperature (above 120° C.). Herein, the condensation and evaporation surfaces are within a short distance from each other, so as to cause the least damage to the oil composition. This technique is also called short-path distillation, and commercial equipment is readily available.

The molecular distillation plant (1) illustrated in FIG. 1, comprises a mixer (2), a pre-heater (3), a degasser (4), a distillation unit (5) and a vacuum pump (6). In accordance to this embodiment, a volatile working fluid comprising an ethyl ester fraction (6% relative to the oil) is added to a fish oil mixture and blended in a mixer (2). The oil mixture is then optionally passed through a means (3) for controlling the oil feed rate (herein about 400 kg/h), such as an ordinary throttling valve. The fish oil mixture is then preheated with a heating means (3) such as a plate heat exchanger to provide a preheated fish oil mixture. The mixture is then passed through a degassing step (4) and admitted into the molecular path distance evaporator (5), a tube (7) including the condensation (8) and evaporation (9) surface.

The stripping process is carried out at a pressure between 0.1 and 0.001 mbar and at a temperature of about 200° C. The fish oil mixture to be concentrated is picked up as it enters the tube (7a) by rotating blades. The blades extend nearly to the bottom of the tube and mounted so that there is a clearance of about 1, 3 mm between their tips and the inner surface of the tube. In addition, the blades are driven by an external motor. The fish oil mixture is thrown against the tube wall and is immediately spread into a thin film and is forced quickly down the evaporation surface. The film flows down by gravity and becomes concentrated as it falls. Heated walls and high vacuum strips off the volatile working fluid together with the environmental pollutants, i.e. the more volatile components (distillate) is derived to the closely positioned internal condenser (8), the less volatile components (residue) continues down the cylinder. The resulting fraction, the stripped fish oil mixture containing at least the fatty acids EPA and DHA is separated and exit through an individual discharge outlet (10).

In a second embodiment a falling film evaporator is used. In falling film evaporators liquid and vapours flow downwards in parallel flow. The liquid to be concentrated, herein the fish oil mixture, is preheated to boiling temperature. The oil mixture enters the heating tubes via a distribution device in the head of the evaporator, flows downward at boiling temperature, and is partially evaporated. This gravity-induced downward movement is increasingly augmented by the co-current vapour flow.

Falling film evaporators can be operated with low temperature differences between the heating media and the boiling liquid, and they also have short product contact times, typically just a few seconds per pass.

In a third embodiment of the invention the process is carried out by a short path distillation, which includes the use of a short path evaporator that integrates the features and advantages of thin film or wiped film evaporators but adds internal condensing for applications. Short path evaporators are widely used in fine and specialty chemicals for thermal separation of intermediates, concentration of high value products, and molecular distillation under fine vacuum conditions. Their key features make them uniquely suitable for gentle evaporation and concentration of heat sensitive products at low pressures and temperatures.

It should be understood that many modifications of the above embodiments of the invention are possible within the scope of the invention such as the latter is defined in the appended claims.

EXAMPLES

The invention will now be illustrated by means of the following non-limiting examples. These examples are set forth merely for illustrative purposes and many other variations of the process may be used. The examples below summarizes some results from different purification of fish oils by molecular distillation.

Equipment and Conditions for Laboratory Experiments

In example 1-3 below decachlorobiphenyl, 0.60 mg/kg, was added to a fish oil composition as a pollutant model substance. The high chlorine content in decachlorobiphenyl ensures that this compound is less volatile than environmental pollutants like PCB, DDT and its metaboites, toxaphenes, dioxins and brominated flame retardants.

Unless otherwise stated, in all the examples the pressure was 0.001 mbar. However, as this is the lower limit of the pressure indicator, the real pressure will vary. That is the reason for somewhat varying results from one example to the next. When the distillation equipment is running under stable conditions, no significant variations are expected. However, this points out that constant pressure is not a very strong condition for carrying out the present invention.

Example 1

The Effect of Adding a Working Fluid

A fish oil composition containing fatty acids on triglyceride form and decachlorobiphenyl (0.60 mg/kg), with or without a working fluid, herein an ethyl ester, 8% relative to fish oil, (the ratio of (volatile working fluid):(fish oil) is about 8:100) was distilled by a laboratory scale molecular distillation at a rate of 600 ml/h and a temperature of 180° C. The used ethyl ester mixture was a by-product (distillate fraction) from production of EPA and DHA ethyl ester concentrates.

TABLE 1

The effect of adding a volatile working fluid

| | Decachlorobiphenyl (mg/kg) | Decachlorobiphenyl (% of start value) |
|---|---|---|
| Without WF | 0.43 | 72 |
| With WF | 0.022 | 3.7 |

*WF = working fluid

The results in table 1 show that addition of a volatile working fluid to a fish oil composition has a surprisingly and dramatic effect on the removal of decachlorobiphenyl. Here, more than 95% of the amount of decachlorobiphenyl has been removed ("stripped" off) from the fish oil mixture by molecular distillation.

Example 2

The Effect of Different Flow Rates

A fish oil composition containing fatty acids in triglyceride form and decachlorobiphenyl (0.60 mg/kg) was added a working fluid in the form of a ethyl ester fraction in the same way as in example 1. The oil mixture was then stripped by a molecular distillation carried out at different flow rates, but at the same temperature (180° C.).

TABLE 2

The effect of different flow rates

| Flow rate (ml/h) | Decachlorobiphenyl (mg/kg) |
|---|---|
| 400 | 0.02 |
| 600 | 0.05 |
| 1000 | 0.20 |

The results given in the table above show that decachlorobiphenyl (and other volatile pollutants) will be flashed off (reduced) more successfully at lower flow rates. However, the results of optimising the flow rates are less important compared to the effect of adding a working fluid, such as a solvent, solvent mixture or a fraction containing an ethyl ester.

Example 3

The Effect of Different Temperatures

Here, an ethyl ester fraction was added to a fish oil composition containing decachlorobiphenyl (0, 60 mg/kg) in the same way as in example 1. The oil mixture was then stripped by molecular distillation at different temperatures.

TABLE 3

The effect of different temperatures

| Temperature (° C.) | Decachlorobiphenyl (mg/kg) |
|---|---|
| 180 | 0.11 |
| 200 | 0.04 |

Table 3 illustrates that an increased temperature gives an improved removal of pollutants, when a volatile working fluid has been added to the oil mixture prior to a molecular distillation. Further, it is important to know that polyunsaturated fatty acids in fish oil are thermo-labile compounds and an increase in temperature is only applicable within strict limits.

For a person skilled in the art it is obvious that the same effect as described in example 1-3 will be achieved according to the invention by using other volatile working fluids, as long as the working fluids are essentially equally or less volatile than the environmental pollutants that is to be separated from the oil or fat mixture.

Example 4

Sardine Oil—Industrial Full Scale Process

This example shows an industrial scale process for decreasing the amount of pollutants in a fish oil mixture, which process comprises a step of adding a volatile working fluid to the fish oil mixture prior to a molecular distillation. 63.9 tons of a sardine oil containing different environmental pollutants was added a volatile working fluid in the form of a fatty acid ethyl ester mixture (ethyl ester of fish oil (8%)) before subjecting it to a molecular distillation process. The molecular distillation process was then carried out at a temperature of 200° C., a pressure of 0.04 mbar and a mixture flow rate of 300 l/h with a heated surface of 3 m$^2$.

After treatment, 61.0 tons of purified product were collected. The results in table 4 show the content of vitamin A(trans-retinol), cholesterol, toxaphenes and dioxins in the sardine oil before and after stripping respectively.

TABLE 4

Toxaphenes and dioxins in a sardine oil before and after stripping

|  | Before stripping | After stripping |
|---|---|---|
| Vitamin A | 15.3 mg/g | 13.0 mg/g |
| Cholesterol | 3.6 mg/g | 1.31 mg/g |
| Toxaphenes | 0.3 mg/g | <0.1 mg/g |
| Dioxins | 4.1 pg/g | 0.34 pg/g |

The results confirm that adding a working fluid to an oil before stripping is effective in reducing the amounts of volatile pollutants at the same time as the concentration of vitamin A, a valuable component in many fish oils, is not seriously affected. This means that this purification method can be used for products that contains vitamin A, e.g. cod liver oil.

In some cases a certain cholesterol level can be of value for some applications of fish oils e.g. for fish feed, especially feed for fish larvae. In these applications it is important to perform a preferential removal only of pollutants.

Example 5

Fish Oil Mixture—Industrial Full Scale Process

This example also shows an industrial full scale process for decreasing the amount of pollutants in a fish oil, which process comprises the steps of adding a volatile working fluid to the fish oil mixture and subjecting the mixture, with the added volatile working fluid, to a molecular distillation processing step, in which environmental pollutants present in the fish oil is separated from the mixture with the volatile working fluid.

30 tons of a fish oil mixture containing different environmental pollutants (see FIG. 2) was added a volatile working fluid in the form of an fatty acid ethyl ester mixture (ethyl ester of fish oil (6%)) before subjecting it to a molecular distillation process. The molecular distillation process was then carried out at a temperature of 200° C., a pressure of 0.005 mbar and a mixture flow rate of 400 kg oil/h with a heated surface of 11 m$^2$.

After treatment, 29.5 tons of purified product were collected. The results are shown in FIG. 2. The results confirms that the content of environmental pollutants in the fish oil mixture was strongly reduced after the stripping process according to the invention. For instance, the content of PCB in the fish oil mixture was reduced with about 98%, the content of PCDD was reduced with approximately 80%, the content of PCDF with about 95% and the amount of hexachlorocyclohexane respectively TE-PCB was almost negligible after stripping. For a person skilled in the art it is obvious that the same effect may be achieved according to the invention by using a volatile working fluid for decreasing an amount of pollutants in some other fat or oil compositions.

Example 6

Salmon Oil

In this example oil from fresh by-products from Atlantic salmon was processed according to the invention. The process according to the invention comprises the steps of adding a volatile working fluid to the oil mixture and further subjecting the mixture, with the added volatile working fluid, to a molecular distillation processing step. 8% working fluid (the ratio of (volatile working fluid):(salmon oil) is here about 8:100) was added to the oil and the distillation process was performed at a pressure of $1\times10^{-3}$ mbar, at a temperature of 180° C. and at a mixture flow rate of 600 ml/hour.

Samples of the oil mixture was analysed before and after distillation respectively, regarding the amount of brominated flame retardants, PCBs and some chlorinated pesticides, see the tables 5 and 6 below.

TABLE 5

Brominated flame retardants, µg/kg, before and after a distillation process

| Brominated flame retardants, µg/kg | Before treatment | After distillation |
|---|---|---|
| BDE 28 | 0.3 | <0.2 |
| BDE 47 | 5.3 | <0.2 |
| BDE 66 | 0.4 | <0.2 |
| BDE 71 | <0.2 | <0.2 |
| BDE 75 | <0.2 | <0.2 |
| BDE 77 | <0.2 | <0.2 |
| BDE 85 | <0.2 | <0.2 |
| BDE 99 | 1.2 | <0.2 |
| BDE 100 | 1.0 | <0.2 |
| BDE 119 | <0.2 | <0.2 |
| BDE 138 | <0.2 | <0.2 |
| BDE 153 | <0.2 | <0.2 |
| BDE 154 | 0.5 | <0.2 |
| BDE 183 | <0.2 | <0.2 |
| BDE 190 | <0.2 | <0.2 |
| Me-TBBP-A | 0.2 | <0.2 |
| HBCD | <1.1 | <1.2 |

TABLE 6

PCB and chlorinated pesticides, µg/kg, before and after distillation

| PCB and chlorinated pesticides, (µg/kg) | Before treatment | After distillation |
|---|---|---|
| CB 28 | <3 | <3 |
| CB 52 | 5 | <3 |
| CB 101 | 11 | <7 |
| CB 118 | <9 | <9 |
| CB 153 | 16 | <7 |
| CB 105 | <3 | <3 |
| CB 138 | 13 | <7 |
| CB 156 | <3 | <3 |
| CB 180 | 4.8 | <4 |
| Dieldrin | 22 | <4 |
| Endrin | <3 | <3 |
| HCB | 12 | <1 |
| α-HCH | 3.8 | <1 |
| γ-HCH | 5.3 | <1 |
| β-HCH | <5 | <6 |
| β-HEPO | <2 | <3 |
| p,p'-DDE | 38 | <3 |

TABLE 6-continued

PCB and chlorinated pesticides, μg/kg, before and after distillation

| PCB and chlorinated pesticides, (μg/kg) | Before treatment | After distillation |
|---|---|---|
| p,p'-DDD | 15 | <3 |
| p,p'-DDT | nd = not detected | <8 |

It is observed that the invention removes almost all of the analysed environmental pollutants to a level below the analytical detection limit.

Additionally, for a person skilled in the art it will be obvious that the same procedure could be used for other marine oils, for example cod liver oil or fish oil intended to be used as a component of feed for farmed fish. Nowadays, commercial fish feed contains high amounts of pollutants and it is therefore of large interest to decrease the amounts of toxic components in the current marine oil before the oil is added to the feed.

Example 7

Removal of PAH's

In this example benzo[a]pyrene (8.36 μg/kg oil) was added to a fish oil composition, that already had been treated according to the invention, in order to remove environmental pollutants. The fish oil composition containing the added benzo[a]pyrene was processed in a similar way and with the same distillation equipment as described in example 1. A volatile working fluid in the form of a fatty acid ethyl ester mixture, 8% working fluid relative to the fish oil, was added to the fish oil composition, before subjecting the composition to a molecular distillation process. The molecular distillation process was carried out at a temperature of 180° C., a pressure of $1 \cdot 10^{-3}$ mbar, and a mixture flow rate of 600 ml oil/h. The concentration of benzo[a]pyrene was analysed before processing and after processing, see table 7.

TABLE 7

The amount of benzo[a]pyrene before and after processing

| | Before processing | After processing |
|---|---|---|
| Benzo[a]pyrene (μg/kg) | 7.9 | 0.77 |

The results given in the table above show that benzo[a]pyrene will be flashed off successfully according to the invention. In this example the concentration of benzo[a]pyrene was reduced with about 90%.

This confirms that adding a volatile working fluid to a fat or an oil composition, at least containing polycyclic aromatic hydrocarbons (PAH's), before a stripping process according to the invention is effective in separating an amount of PAH's from the start fat or oil composition together with the volatile working fluid.

Example 8

A working fluid consisting of ethyl esters of fish oil (8%) was added to an oil produced from farmed salmon. A distillation process was carried out under the same conditions as in example 1 and a distillate fraction of 8.3% was collected. The acid value of the residual oil was reduced from 0.4 mgKOH/g before distillation to 0.1 mgKOH/g after distillation and the oil was analysed for contaminants before and after processing.

TABLE 8

Salmon oil. Content of Indicator-PCBs (μg/kg) before and after processning.

| | CB-28 | CB-52 | CB-101 | CB-118 | CB-153 | CB-105 | CB-138 | CB-156 | CB-180 |
|---|---|---|---|---|---|---|---|---|---|
| Before | <3 | 5 | 11 | <9 | 16 | <3 | 13 | <3 | 4.8 |
| After | <3 | <3 | <7 | <9 | <7 | <3 | <7 | <3 | <4 |

TABLE 9

Salmon oil. Content of organochlorine pesticides (μg/kg) before and after processing

| | Dieldrin | Endrin | HCB | a-HCH | y-HCH | b-HCH | b-HEPO | pp_DDE | pp_DDD | pp_DDT |
|---|---|---|---|---|---|---|---|---|---|---|
| Before | 22 | <3 | 12 | 3.8 | 5.3 | <6 | <3 | 38 | 15 | <8 |
| After | <4 | <3 | <1 | <1 | <1 | <6 | <3 | <3 | <3 | <8 |

The results show that adding a volatile working fluid prior to a stripping (distillation) process is effective in decreasing the amount of organo-chlorine pesticides in a fish oil composition. In addition, the volatile working fluid also facilitates removal of free fatty acids in the oil. Therein the acid value was decreased with 75%, i.e. from 0.4 to 0.1. It is hereby possibly to decrease the amount of environmental pollutants and to reduce the amount of free fatty acids in an oil or a fat at the same time and in the same process.

Example 9

Removal of Free Fatty Acids

A fish oil purchased for production of fish feed was distilled by a molecular distillation process under the same conditions as given in example 1 and the start oil had an acid value of 6.8 mgKOH/g. After removal of a distillate corresponding to 4.3% by weight, the acid value of the residual oil was reduced to 0.2 mgKOH/g and the amount of environmental pollutants in the start oil was decreased.

In an identical distillation procedure, an oil with an acid value of 20.5 mgKOH/g was distilled. After removal of a distillate of 10.6% the acid value was reduced to about 1.0 mgKOH/g and the amount of environmental pollutants in the start oil were decreased.

Due to the fact that the stripping process in example 8 also facilitates removal of free fatty acids in the oil and that the free fatty acids are volatile it can be expected that even oils with a low quality, i.e. a high content of free fatty acids, can be treated successfully according to the invention. An example of oils with low quality is silage oils or oils that have been stored or transported for a long period of time. Fish oils with low quality may be used for production of fish feed.

This example therefore shows that a stripping process for decreasing the amount of environmental pollutants in a mixture comprising at least a fat or an oil with a high content of free fatty acids (a low quality oil or fat) is effective since the free fatty acids in the oil or fat act as a working fluid. Further, the free fatty acids in the oil or fat also contributes to an additive effect in the stripping process by partially acting as an internal working fluid (or by being an active part of the working fluid) in the stripping process.

A person known in the art will also realise that the same stripping effect can be obtained by adding a volatile working fluid containing a similar volume of suitable free fatty acids to an oil or fat containing environmental pollutants in order to decrease the amount of environmental pollutants in the fat or oil.

Example 10

Removal of Toxic Components From a Ricinus Oil

This example shows a process for decreasing the amount of toxic compounds in a ricinus oil (castor oil, oil from the seeds of *Ricinus communis L. Euphorbiaceae*), which process comprises the steps of adding a volatile working fluid to a ricinus oil mixture and subjecting the mixture, with the added volatile working fluid, to a molecular distillation processing step, in which traces of ricinine from the ricinus oil is separated from the mixture with the volatile working fluid.

Firstly, 8% of a working fluid, (the ratio of (volatile working fluid):(ricinus oil) is here about 8:100) a distilled fraction of ethyl esters from a fish oil, was added to a ricinus oil prior to a distillation processing step. Secondly, the ricinus oil mixture was distilled in a molecular distillation process at a temperature of 170° C., at a pressure of $10^{-3}$ mbar and at a mixture flow of 500 ml/min. The concentration of toxic compounds were analysed before and after treatment. This analysis showed that the concentration of ricinine was substantially reduced compared to the concentration in the starting ricinus oil. This shows that it is possible to reduce traces of toxic components in a ricinus oil according to the invention, as long as the used volatile working fluid is essentially equally or less volatile than the components that is to be separated from the ricinus oil. Further, ricinus oil is used in both medicinal and cosmetic applications and the reduction of the existing trace levels of ricinin has commercial value.

The invention claimed is:

1. A process for decreasing the amount of environmental pollutants in a mixture comprising a fat or an oil, wherein said mixture comprises a pharmaceutical composition, said process comprising the steps:

(a) adding a volatile working fluid to the fat or oil mixture, wherein the volatile working fluid comprises at least one fluid chosen from fatty acid esters, fatty acid amides, and hydrocarbons, and (b) subjecting the mixture of step (a) to at least one stripping processing step, wherein an amount of said environmental pollutants is separated from the mixture together with the volatile working fluid; and wherein said pharmaceutical composition is not a health supplement.

2. The process according to claim 1, wherein the volatile working fluid with the environmental pollutants is derived to a condenser.

3. The process according to claim 1, wherein the volatile working fluid is equally or less volatile than the environmental pollutants that are to be separated from the fat or oil mixture.

4. The process according claim 1, wherein the at least one fluid chosen from fatty acid esters, fatty acid amides, and free fatty acids is obtained from at least one source chosen from a vegetable fat, a vegetable oil, a microbial fat, a microbial oil, an animal fat, an animal oil, and a bio-diesel.

5. The process according to claim 4, wherein the at least one of an animal fat and animal oil is chosen from a fish oil and an oil obtained from sea mammals.

6. The process according to claim 1, wherein the volatile working fluid comprises at least one fatty acid ester comprising $C_{10}$-$C_{22}$ fatty acids and $C_1$-$C_4$ alcohols, or a combination of at least two fatty acid esters, each comprising $C_{10}$-$C_{22}$ fatty acids and $C_1$-$C_4$ alcohols.

7. The process according to claim 1, wherein the fat or oil is obtained from at least one chosen from a vegetable fat, a vegetable oil, a microbial fat, a microbial oil, an animal fat, and an animal oil.

8. The process according to claim 7, wherein the fat or oil is a marine oil.

9. The process according to claim 8, wherein the marine oil is obtained from at least one of fish and sea mammals, and wherein said marine oil comprises at least one fatty acid chosen from saturated and unsaturated fatty acids in the form of triglycerides.

10. The process according to claim 8, wherein the content of brominated flame retardants in the marine oil as measured by the concentration of BDE 47 is reduced to less than 5.3 μg/kg.

11. The process according to claim 10, wherein the content of brominated flame retardants in the marine oil as measured by the concentration of BDE 47 is reduced to less than 0.2 μg/kg.

12. The process according to claim 8, wherein the content of dioxin-like polychlorinated biphenyls in the marine oil as measured by the concentration of TE-PCB is reduced to less than 22.6 pg/g (TE/WHO).

13. The process according to claim 8, wherein the content of dioxins in the marine oil as measured by the concentration of the total of PCDD and PCDF is reduced to less than 4.65 pg/g (TE/WHO).

14. The process according to claim 1, wherein the ratio of volatile working fluid to the fat or oil ranges from 1:100 to 15:100.

15. The process according to claim 14, wherein the ratio of volatile working fluid to the fat or oil ranges from 3:100 to 8:100.

16. The process according to claim 1, wherein the at least one stripping processing step is carried out at a temperature ranging from 120° C. to 270° C.

17. The process according to claim 16, wherein the at least one stripping processing step is carried out at a temperature ranging from 150° C. to 200° C.

18. The process according to claim 1, wherein the at least one stripping processing step is carried out at a pressure less than 1 mbar.

19. The process according to claim 1, wherein said at least one stripping processing step is chosen from short path distillation, short path evaporation, thin-film distillation, thin-film evaporation, falling-film distillation, falling-film evaporation, and molecular distillation.

20. The process according to claim 19, wherein the at least one stripping processing step is thin-film evaporation carried out at a mixture flow rate ranging from 10 kg/h·m$^2$ to 300 kg/h·m$^2$.

21. The process according to claim 9, further comprising the step of concentrating the marine oil.

* * * * *

UNITED STATES PATENT AND TRADEMARK OFFICE
CERTIFICATE OF CORRECTION

| | |
|---|---|
| PATENT NO. | : 7,718,698 B2 |
| APPLICATION NO. | : 12/113356 |
| DATED | : May 18, 2010 |
| INVENTOR(S) | : Harald Breivik et al. |

Page 1 of 1

It is certified that error appears in the above-identified patent and that said Letters Patent is hereby corrected as shown below:

On the Title Page, Item (54), in the Title, line 3, after "OR A FAT", insert

--, A VOLATILE ENVIRONMENTAL POLLUTANTS DECREASING WORKING FLUID, A HEALTH SUPPLEMENT, AND AN ANIMAL FEED PRODUCT--.

On the Title Page, Item (57), in the Abstract, line 7, "amid," should read --amide,--.

On the Title Page, Item (57), in the Abstract, line 8, "hydro-carbon," should read --hydrocarbon,--.

In claim 4, column 20, line 18, "according claim 1," should read --according to claim 1,--.

In claim 4, column 20, lines 19-20, "and free fatty acids" should read --free fatty acids, and hydrocarbons--.

Signed and Sealed this
First Day of May, 2012

David J. Kappos
*Director of the United States Patent and Trademark Office*

UNITED STATES PATENT AND TRADEMARK OFFICE
CERTIFICATE OF CORRECTION

PATENT NO. : 7,718,698 B2  
APPLICATION NO. : 12/113356  
DATED : May 18, 2010  
INVENTOR(S) : Harald Breivik et al.

Page 1 of 1

It is certified that error appears in the above-identified patent and that said Letters Patent is hereby corrected as shown below:

On the Title Page, Item (54) and at Column 1, line 3 in the Title, after "OR A FAT", insert --, A VOLATILE ENVIRONMENTAL POLLUTANTS DECREASING WORKING FLUID, A HEALTH SUPPLEMENT, AND AN ANIMAL FEED PRODUCT--.

On the Title Page, Item (57), in the Abstract, line 7, "amid," should read --amide,--.

On the Title Page, Item (57), in the Abstract, line 8, "hydro-carbon," should read --hydrocarbon,--.

In claim 4, column 20, line 18, "according claim 1," should read --according to claim 1,--.

In claim 4, column 20, lines 19-20, "and free fatty acids" should read --free fatty acids, and hydrocarbons--.

This certificate supersedes the Certificate of Correction issued May 1, 2012.

Signed and Sealed this  
Twenty-ninth Day of May, 2012

David J. Kappos  
*Director of the United States Patent and Trademark Office*